(12) United States Patent
Cho

(10) Patent No.: US 9,241,624 B2
(45) Date of Patent: Jan. 26, 2016

(54) BINOCULAR VISUAL SIMULATOR

(71) Applicant: HUVITZ CO., LTD., Gyeonggi-Do (KR)

(72) Inventor: Minsoo Cho, Seoul (KR)

(73) Assignee: HUVITZ CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/519,433

(22) Filed: Oct. 21, 2014

(65) Prior Publication Data

US 2015/0116666 A1    Apr. 30, 2015

(30) Foreign Application Priority Data

Oct. 31, 2013 (KR) .................... 10-2013-0130950
Oct. 31, 2013 (KR) .................... 10-2013-0130958

(51) Int. Cl.
*A61B 3/02* (2006.01)
*A61B 3/10* (2006.01)
*A61B 3/032* (2006.01)
*A61B 3/18* (2006.01)

(52) U.S. Cl.
CPC .............. *A61B 3/1015* (2013.01); *A61B 3/032* (2013.01); *A61B 3/185* (2013.01)

(58) Field of Classification Search
CPC ........ A61B 3/1015; A61B 3/032; A61B 3/08; A61B 3/18; A61B 3/185
USPC .................. 351/212, 237, 239, 240, 243, 245
See application file for complete search history.

(56) References Cited

PUBLICATIONS

Darryl Meister Abom "Wavefront Aberrations and Spectacle Lenses Part One" Dispensing Optics, Jan. 2010, pp. 4-12.

*Primary Examiner* — Huy K Mai
(74) *Attorney, Agent, or Firm* — Nath, Goldberg & Meyer; Jerald L. Meyer; Tanya E. Harkins

(57) ABSTRACT

Disclosed is a binocular visual simulator for correcting eyeball aberration by using adaptive optics to form a chart image on both eyes. The binocular visual simulator includes; a chart-projecting unit for producing a chart light; an adaptive optics element for changing the chart light in accordance with wavefront aberration measured for both eyes; a beam splitter for dividing the changed chart light into two chart lights; a left eye correction unit for changing the divided chart light in accordance with wavefront aberration of the left eye so that the chart light is focused on a retina of the left eye; and a right eye correction unit for changing the divided chart light in accordance with wavefront aberration of the right eye so that the chart light is focused on a retina of the right eye.

22 Claims, 14 Drawing Sheets

Fig. 1
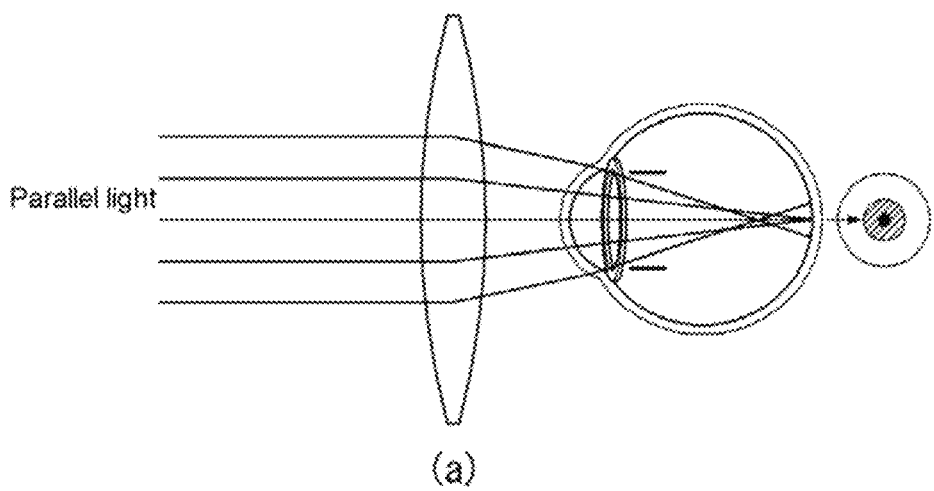
(a)
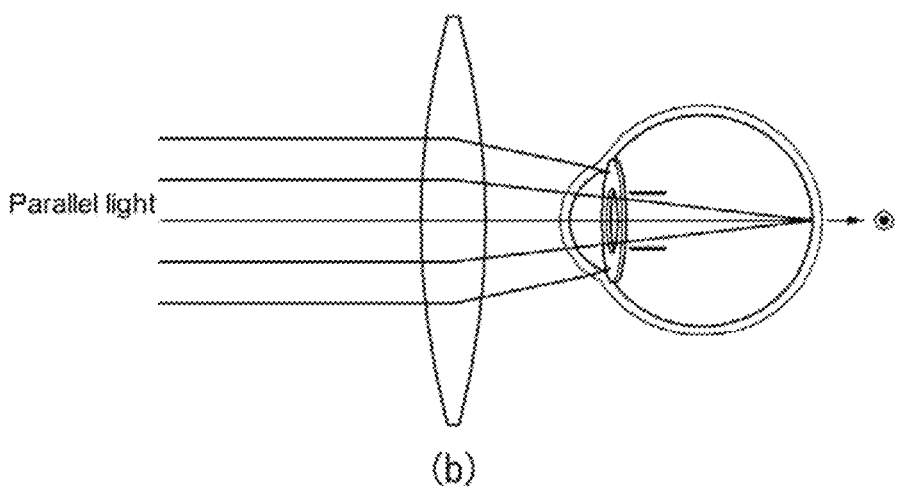
(b)

Fig. 5
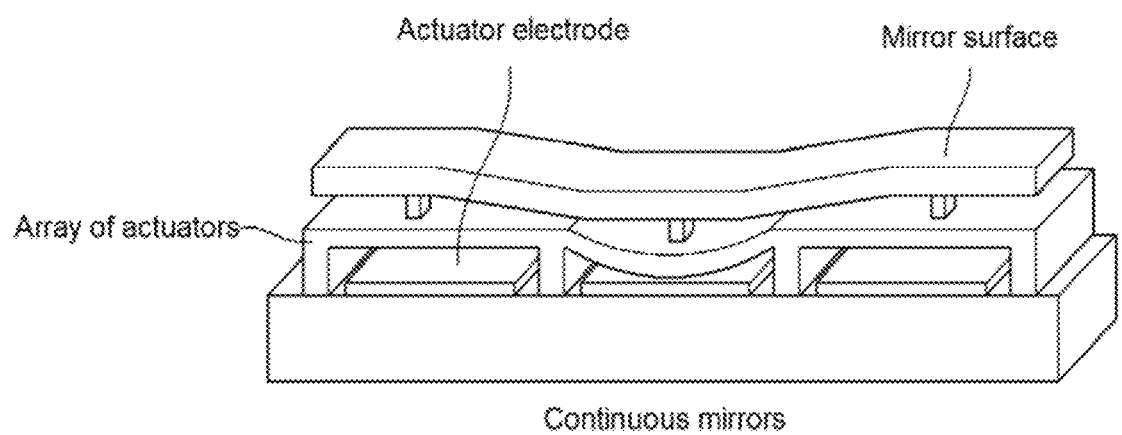
Continuous mirrors
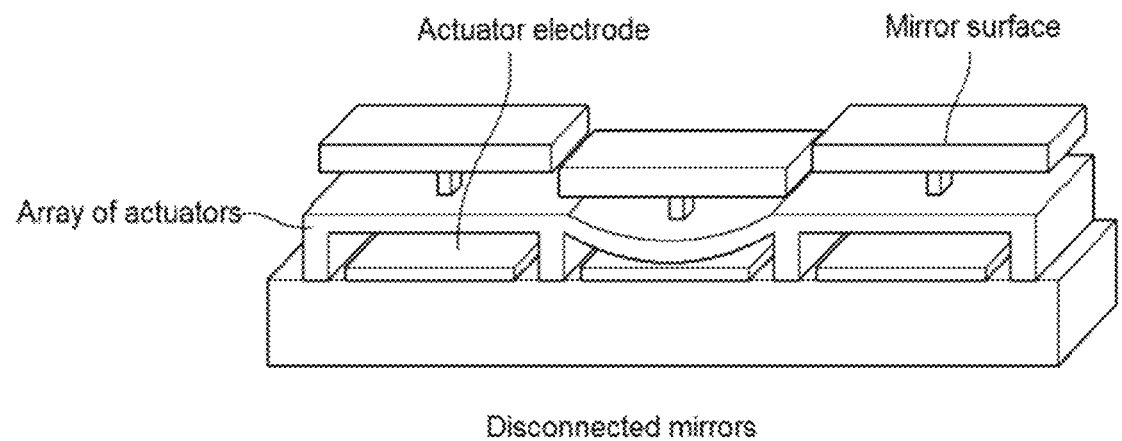
Disconnected mirrors

Fig. 6
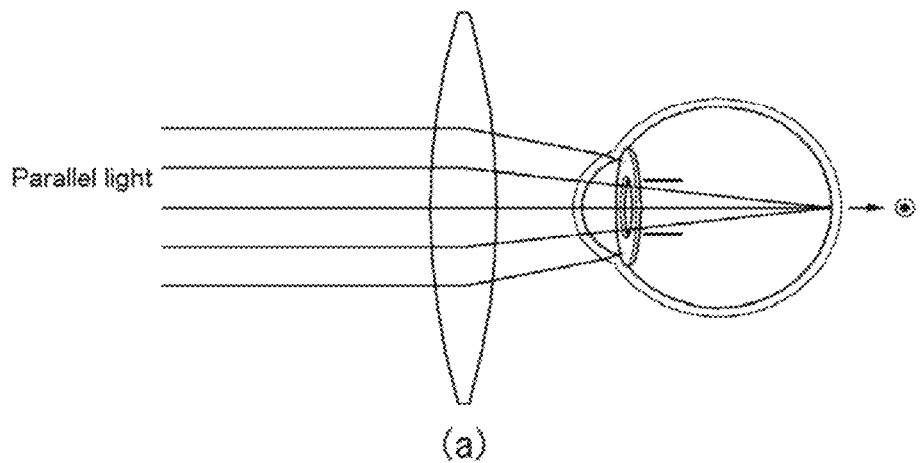
(a)
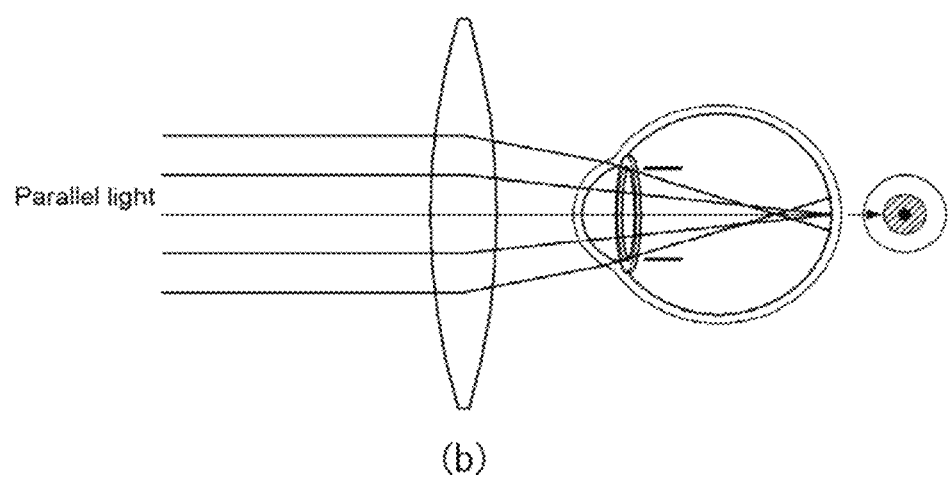
(b)
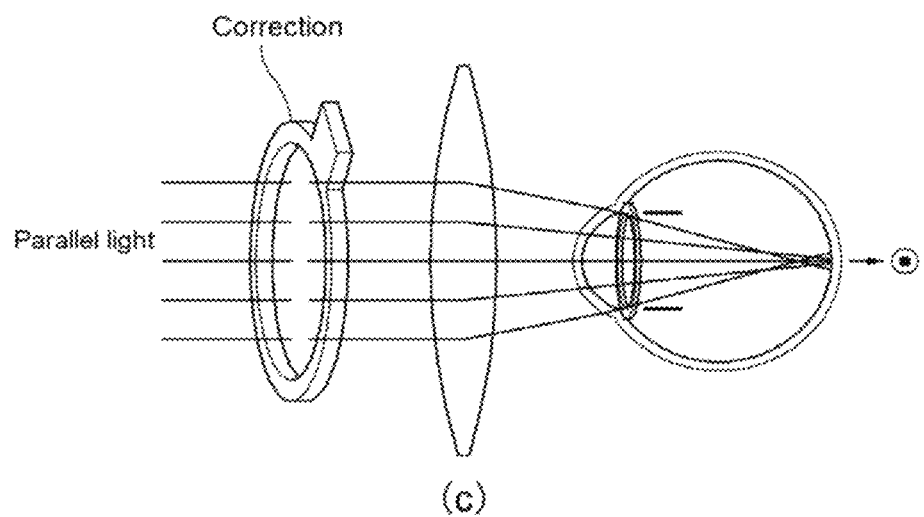
(c)

BINOCULAR VISUAL SIMULATOR

CROSS REFERENCE TO RELATED APPLICATION

This application claims the priority benefits of Korean Patent Application Nos. 10-2013-0130950 and 10-2013-0130958 both filed on Oct. 31, 2013, the entire contents of which are incorporated herein by reference.

BACKGROUND OF THE INVENTION

1. Technical Field

This invention relates to a binocular visual simulator and, more particularly, to a binocular visual simulator for correcting eyeball aberration by using adaptive optics to form a chart image on both eyes.

2. Description of the Related Art

In order to solve the inconveniences of wearing glasses for eyesight correction, keratectomy, such as LASIK (laser in-situ keratomileusis), LASEK (laser assisted sub-epithelial keratomileusis), or PRK (photorefractive keratectomy) using excimer laser, prevails. However, even after keratectomy is performed, there frequently occurs that eyesight is not greatly improved, or light spreading (diffusion of focal point) is generated at night due to a side effect of the keratectomy though there is no problem in daytime eyesight.

When pupils are constricted in bright light condition as in the daytime, light passing through a portion near the center of the cornea is chiefly focused on the retina because light incident to a peripheral portion which is deviated from the center of the cornea is blocked by the pupil, thereby forming a clear image. When the pupil has dilated because the surroundings are dark as at night, light passing through the center of the cornea is focused on the retina, while light passing through the peripheral portion of the cornea is focused ahead of the retina. As a result, an image is not clear and looks opaque or light looks spread. The reason for these results from spherical aberration.

However, there is a problem in that a patient may have a burden of a surgical operation because the patient is unaware that how much will do light spreading occur at night before the patient is subject to a keratectomy operation.

For example, if eyesight is measured using an automatic eyesight measurement unit (e.g., a phoropter), some among a plurality of lenses are alternately inserted between the cornea and a chart, and eyesight is measured while watching a chart whose diopter has been corrected. Since the predetermined lenses correct only a diopter corresponding to low order aberration, a clear focus is formed on the retina when the pupil contracts as illustrated in (b) of FIG. 1, but a clear focus is not formed on the retina due to the aberration of a peripheral portion when the pupil dilates as illustrated in (a) of FIG. 1. Furthermore, there is no scheme for correcting high order aberration, that is, a scheme for focusing an image on the retina of a patient in the state in which high order aberration has been corrected, because only a diopter is corrected using the automatic eyesight measurement unit.

Furthermore, since a chart for eyesight measurement (or a chart) outputs an image including dark letters in a bright and white background, the pupil contracts when an image of the chart enters an eyeball, thereby making it difficult to measure eyesight in the state in which the pupil has dilated.

Furthermore, in eyesight measurement for a conventional eyesight correction operation, there is a problem in that it is difficult to precisely measure binocular eyesight simultaneously because eyesight measurement is performed on each of both eyes.

SUMMARY OF THE INVENTION

Accordingly, this invention has been made keeping in mind the above problems occurring in the prior art, and an object of the present invention is to provide a simulator that enables a person whose eyes will be tested to previously experience an image having corrected high order aberration.

Another object of the present invention is to provide a simulator capable of eyesight measurement in a state in which the pupil has dilated.

Yet another object of the present invention is to provide a simulator capable of performing eyesight measurement of both eyes at the same time.

In accordance with an embodiment of the present invention, there is provided a binocular visual simulator comprising: a chart-projecting unit for producing a chart light including a chart image to be focused on a retina; an adaptive optics element for changing the chart light of the chart-projecting unit in accordance with wavefront aberration measured for a left eye and a right eye; a beam splitter for dividing the chart light changed by the adaptive optics element into two chart lights; a left eye correction unit for changing the chart light divided by the beam splitter in accordance with wavefront aberration of the left eye so that the chart light is focused on a retina of the left eye; and a right eye correction unit for changing the chart light divided by the beam splitter in accordance with wavefront aberration of the right eye so that the chart light is focused on a retina of the right eye. Each of the left eye correction unit and the right eye correction unit includes a shutter for controlling projection of the chart light to the left eye and the right eye. The shutter of the left eye correction unit and the shutter of the right eye correction unit are alternately turned on (on-state) and turned off (off-state).

In one embodiment, each of the left eye correction unit and the right eye correction unit includes an alignment optical system for detecting an alignment of a center of cornea of the corresponding eyeball with a center of a light outputted from the corresponding eye correction unit.

In one embodiment, the alignment optical system includes an alignment lighting for symmetrically radiating invisible rays toward the eyeball, a beam splitter for reflecting the chart light and for transmitting a reflected light of the invisible rays reflected at the cornea of the eyeball and a light detection element for detecting the reflected light.

In one embodiment, each of the left eye correction unit and the right eye correction unit includes an actuator for moving the corresponding eye correction unit so that the center of each cornea is aligned with a center of the light of the left eye correction unit and the right eye correction unit.

In one embodiment, each of the left eye correction unit and the right eye correction unit includes a plurality of lenses for compensating for low order aberration of wavefront aberration which is measured for the corresponding eyeball.

In one embodiment, the plurality of lenses is a zoom lens for controlling a defocusing of incident light.

In one embodiment, zoom magnification of the zoom lens is additionally controlled in accordance with a distance between the corresponding eye correction unit and the corresponding cornea of an eyeball.

In one embodiment, zoom magnification of the zoom lens is additionally controlled in accordance with a distance between the beam splitter and the corresponding eye correction unit in left and right direction.

In one embodiment, the adaptive optics element compensates for high order aberration among the wavefront aberrations measured for the left eye and the right eye, thereby changing a wavefront of the chart light.

In one embodiment, the adaptive optics element is a deformable mirror whose surface is changed by a plurality of actuators.

In one embodiment, the adaptive optics element is operated with being synchronized with the shutter of the left eye correction unit and the shutter of the right eye correction unit.

In one embodiment, the adaptive optics element operates in accordance with the wavefront aberration of the left eye when the shutter of the left eye correction unit is open and the adaptive optics element operates in accordance with the wavefront aberration of the right eye when the shutter of the right eye correction unit is open.

In one embodiment, the chart-projecting unit produces either the chart light including a chart image in which black letters are on white background or the chart light including a chart image in which white letters are on black background.

In accordance with other embodiment of the present invention, there is provided a binocular visual simulator comprising: a main body including an adaptive optics element for changing a chart light including chart images to be focused on retinas of a left eye and a right eye in accordance with wavefront aberration measured for the left eye and the right eye, and a left eye correction unit and a right eye correction unit for further changing the chart light and projecting the changed chart lights to a retina of the left eye and a retina of the right eye, respectively; a first link downwardly extended from the center of the main body and having a guide slot formed in the first link; a vertical support hingedly connected to the main body; and, a second link hingedly connected to the vertical support and having a sliding member being moved along the guide slot.

In one embodiment, the vertical support is hingedly connected to the main body at a first position that is a center of the main body in the right and left directions and that is a center of the left eye correction unit and the right eye correction unit in the vertical direction.

In one embodiment, the guide slot is formed in a vertically extended shape.

In one embodiment, when the sliding member moves in the right and left directions along the guide slot, the main body is tilted from horizontal position.

In one embodiment, the binocular visual simulator further comprises a left transfer part for moving the left eye correction unit in the left and right directions; and a right transfer part for moving the right eye correction unit in the left and right directions.

In one embodiment, the left transfer part and the right transfer part are linearly actuated by a screw rotated by a rotator motor.

In one embodiment, the binocular visual simulator further comprises a base; and a movable stand which moves in a horizontal direction on the base, and the base comprises a face support for supporting a forehead and jaw of a person, and the vertical support is fixed to the movable stand.

In one embodiment, the binocular visual simulator further comprises a sensor for measuring an angle and direction of the left eye correction unit and/or the right eye correction unit which are tilted by the second link.

In one embodiment, the wavefront aberration of the left eye and/or the right eye is modified in accordance with the angle and direction measured by the sensor, and the chart light is changed in accordance with the modified wavefront aberration.

Accordingly, there is an advantage in that a burden of an operation can be reduced because a patient who will be subject to keratotomy experiences a state after the operation in advance.

Furthermore, simulations can be performed at night situations in which dazzling or light spreading may occur.

Furthermore, a cost can be reduced because both eyes can be simulated using only a single adaptive optics element required to correct high order aberration.

BRIEF DESCRIPTION OF THE DRAWINGS

FIG. 1 is a diagram illustrating that aberration is generated by a dilation of pupils even when a correction lens having a diopter is used;

FIG. 5 is a diagram illustrating an adaptive mirror which change a displacement of a surface;

FIG. 6 is a diagram illustrating an example in which aberration is minimized using a deformable optical element in a state in which the pupil has dilated;

DETAILED DESCRIPTION

Hereinafter, binocular visual simulators in accordance with some exemplary embodiments of the present invention are described in detail with reference to the accompanying drawings.

Figure 2:
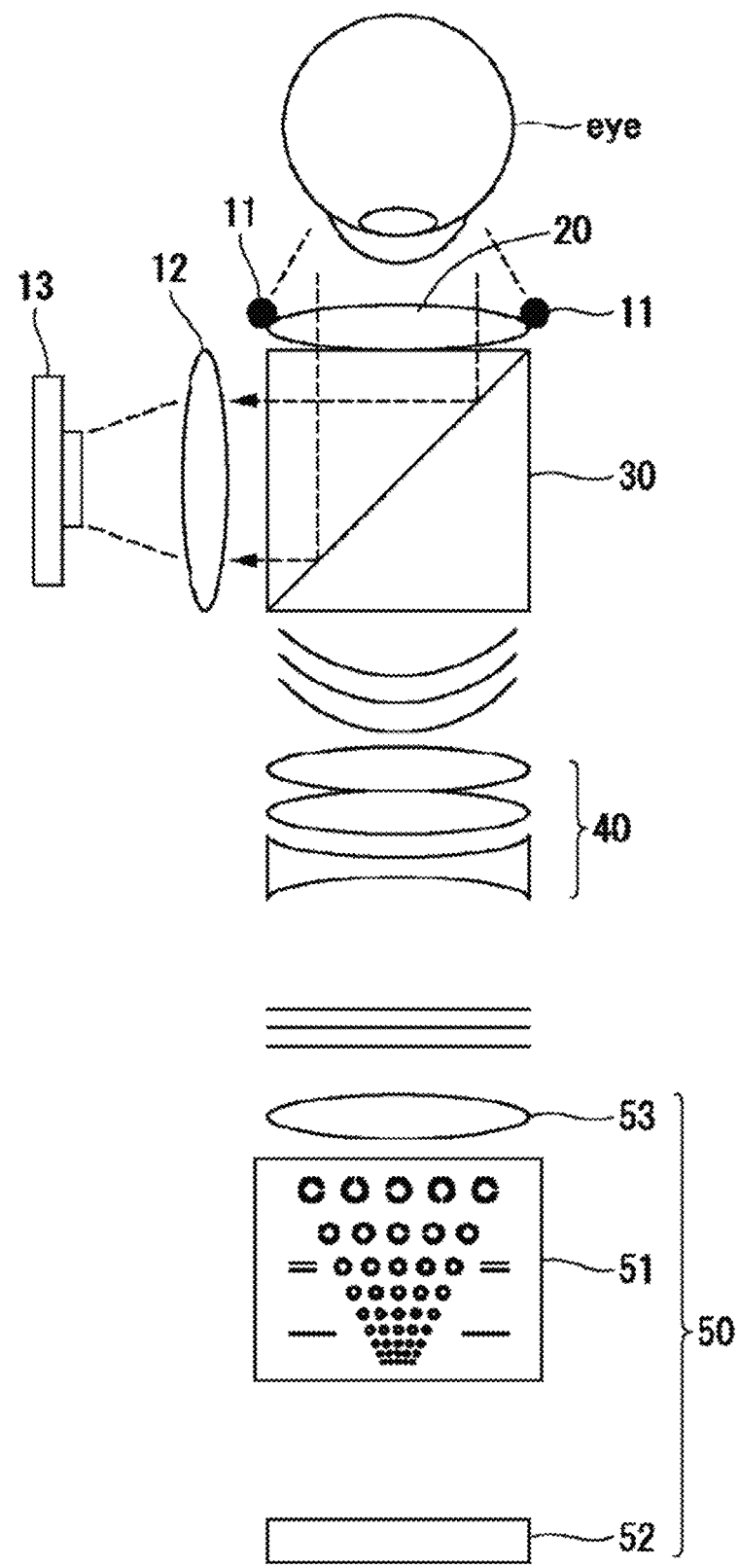
FIG. 2 is a diagram illustrating an operation of a configuration for aligning an eye in a known visual simulator for eyesight tests.
Figure 3:
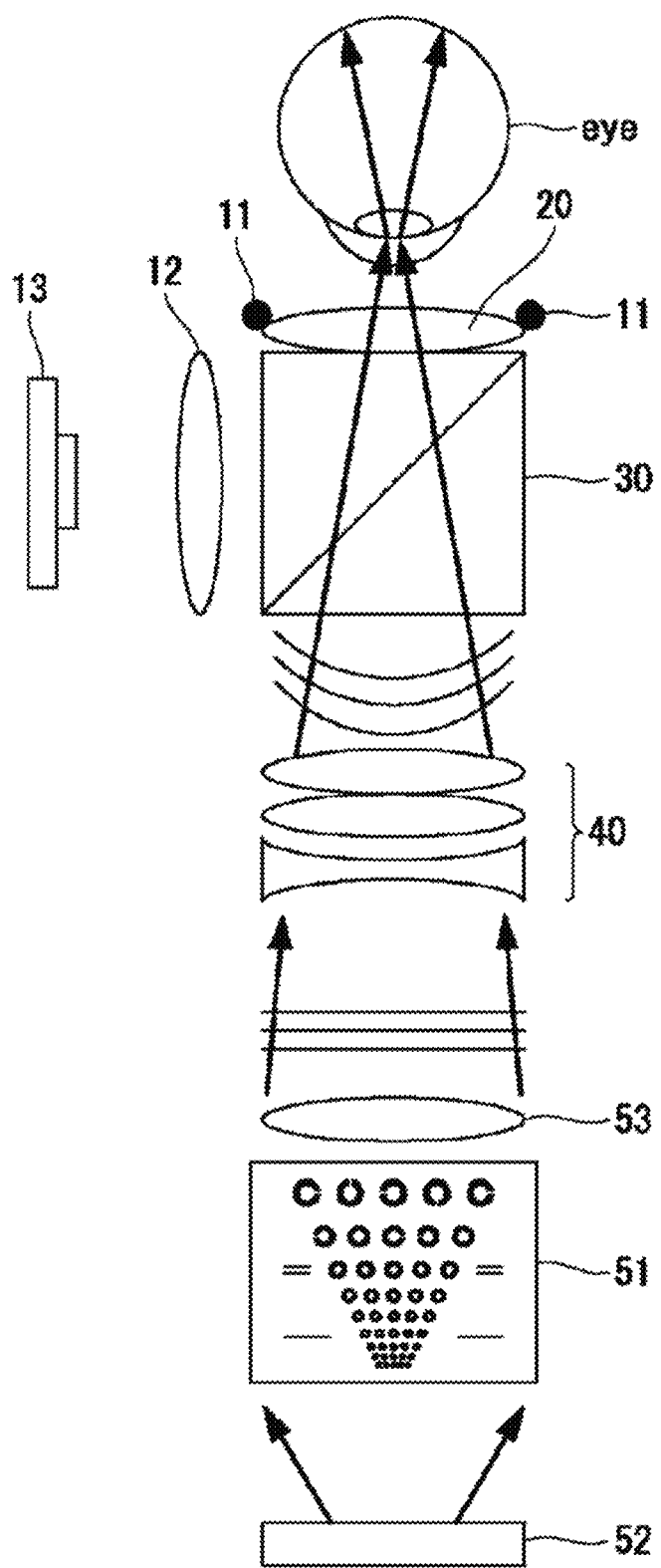
FIG. 3 is a diagram illustrating a flow of beam in which a chart is focused on a retina in the configuration of a known visual simulator for eyesight tests.

FIG. 2 is a diagram illustrating an operation of a configuration for aligning an eye in a known visual simulator for eyesight tests, and FIG. 3 is a diagram illustrating a flow of beam in which a chart is focused on a retina in the configuration of a known visual simulator for eyesight tests.

The visual simulator may be configured to include an alignment optical system configured to align an eyeball and the visual simulator and a focusing optical system configured to focus an chart image on the retina of the eyeball.

The alignment optical system is for adjusting the distance between the visual simulator and the cornea of the eyeball and/or for aligning the center of light output by the visual simulator and the center of the cornea. The alignment optical system is configured to project special signal light for obtaining alignment information, for example, light of a specific shape including an alignment index onto the eyeball, to detect signal light reflected from the eyeball, to compute information about the location of the signal light in accordance with the signal light detected by the operation unit of the visual simulator, and to control the location of the visual simulator using the computed information.

To this end, the alignment optical system may be configured to include pieces of alignment lighting 11 configured to symmetrically radiate invisible infrared rays toward the eyeball, a focusing lens 12 configured to collect pieces of reflected light reflected from the cornea after the light is radiated by the pieces of alignment lighting 11, and a light detection element 13 configured to detect the reflected light.

The visual simulator may be configured to further include an object lens 20 configured to focus chart light, including an image of the chart, on the eyeball, a beam splitter 30 configured to reflect the reflected light (i.e., infrared rays) radiated by the pieces of alignment lighting 11 and then reflected from the cornea of the eyeball and to transmit the chart light (i.e., a visible ray) including an image of the chart that will be focused on the retina of the eyeball, a correction lens 40 configured to control eyesight of the eyeball, and a chart-projecting unit 50 configured to output the chart light including an image of the chart. The chart-projecting unit 50 may be configured to include the chart 51 configured to include an image for eyesight measurement, chart lighting 52 configured to radiate light to the chart 51 so that the chart light is generated, and a chart lens 53 configured to control the degree of divergence or convergence of the chart light.

As illustrated in FIG. 2, the pieces of alignment lighting 11 of the alignment optical system radiate pieces of alignment light of a symmetrical form (i.e., light including information about an alignment index) toward the eyeball. Light reflected from the cornea of the eyeball is reflected from the beam splitter 30 via the object lens 20, condensed by the focusing lens 12, focused on the two-dimensional light detection element 13, and converted into an electrical signal. The light detection element 13 computes the shape, size, location, and focusing degree of a detected two-dimensional alignment index image. The light detection element 13 may control the distance between the visual simulator and the eyeball in accordance with the computed shape, size, location, and focusing degree and/or may reconcile light output by the visual simulator with the center of the cornea.

Furthermore, as illustrated in FIG. 3, chart light that is output by the chart-projecting unit 50 and that includes an image of the chart 51 forms a plane wave having a constant wavefront and becomes convergent light through the correction lens 40 configured to control eyesight of the eyeball, that is, a diopter. Thereafter, the light passes through the beam splitter 30 and the object lens 20, and thus an image of the chart is focused on the retina via the cornea of the eyeball.

The known visual simulator of FIGS. 2 and 3 does not disclose a scheme for enabling an examinee to experience an image having corrected high order aberration in an optical system that forms eyesight of the examinee because only low order aberration, such as spherical aberration, is corrected by the correction lens 40 for defocusing chart light and only whether or not the examinee well sees an image of the chart is checked.

Figure 4:
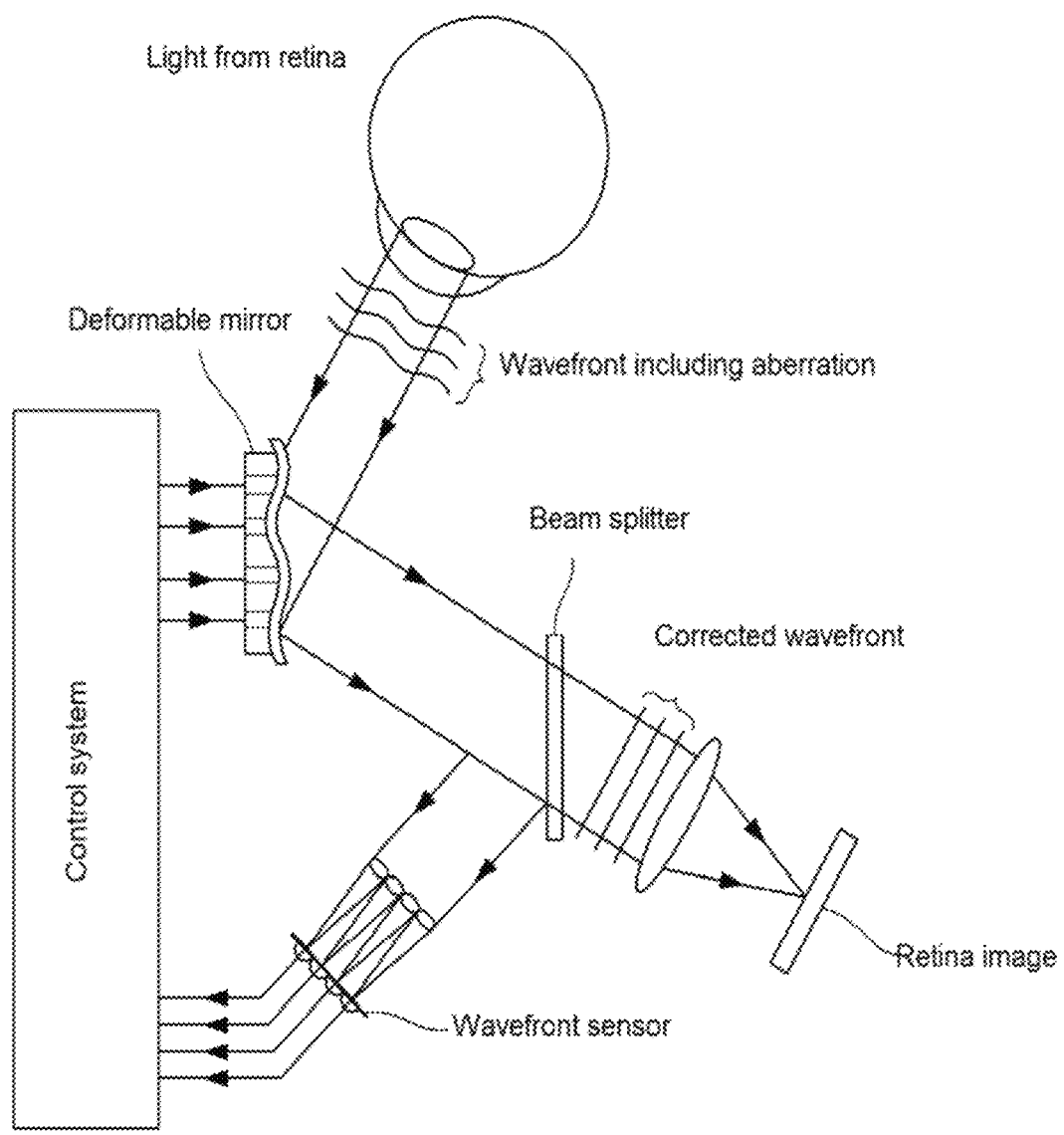
FIG. 4 is a diagram illustrating a configuration of an adaptive optics system applied to wavefront analyses of an optical system configured to form eyesight of an eyeball.

FIG. 4 is a diagram illustrating the configuration of an adaptive optics system applied to wavefront analyses of an optical system configured to form eyesight of an eyeball.

The adaptive optics system is an apparatus configured to measure high order aberration of an eye through a wavefront aberration analyzer and to capture an eyeball image through an adaptive optics element. The adaptive optics system includes an adaptive mirror, a wavefront sensor, a beam splitter, a focusing lens, an image sensor, and a control unit, and may obtain an image of the retina having corrected aberration.

Light containing aberration that is radiated from the retina, is reflected from a deformable mirror whose surface may be deformed, and then form an image of the retina on the high-resolution image sensor via the beam splitter and the focusing lens.

Furthermore, the light reflected from the deformable mirror is reflected from the beam splitter and then focused on the wavefront sensor. For example, a Hartmann-shack sensor may be used as the wavefront sensor. The control unit may compute aberration (i.e., a Zernike coefficient) from the eyeball using the Hartmann-shack sensor.

The aberration of the light is corrected by driving a plurality of actuators for controlling a surface of the deformable mirror by using the Zernike coefficient. Accordingly, an image of the retina having corrected aberration may be obtained through the image sensor.

FIG. 4 illustrates that light emitted from an eyeball includes aberration and the wavefront of the light is winding, but after the light is reflected from the deformable mirror, the aberration of the light has been corrected and the wavefront of the corrected light is parallel to both a temporally adjacent wavefront and a spatially adjacent wavefront.

An adaptive optics system, such as that of FIG. 4, may be used in ophthalmic equipment, such as Optical Coherence Tomography (OCT) and Scanning Laser Ophthalmoscope (SLO).

FIG. 5 is a diagram illustrating an adaptive mirror which may change a displacement of a surface.

The adaptive mirror may include a liquid crystal spatial light modulator, a micro-electro-machined (MEMs) membrane mirror, an MEMs segmented mirror, a bimorph deformable mirror, and an electrostatic membrane deformable mirror.

In the adaptive mirror of FIG. 5, a plurality of actuators (e.g., piezoelectric actuators) which may be moved in a direction vertical to a surface of the adaptive mirror may change a displacement or form of a surface of the adaptive mirror. A mirror on the upper side of FIG. 5 has a form in which a reflected surface having a continuous mirror surface not having disconnection, and a mirror on the lower side of FIG. 5 has a form in which a surface of the mirror is disconnected in accordance with each actuator.

The adaptive mirror or the deformable mirror may include the actuators in a two-dimensional form, for example, 7×7 or 8×8. Each of the actuators may move a surface of the mirror in accordance with an amount that at least partially corresponds to voltage or an electric current when the voltage or electric current is applied to the electrode of the actuator. The range that the actuator is movable may be several um, and the response speed of the actuator may be about ms.

If the adaptive mirror is used in an optical system, precision and response speed can be improved because the number of parts that need to be moved is reduced, for example, a 5 diopter or higher may be corrected, and high order aberration may also be corrected.

FIG. 6 is a diagram illustrating an example in which aberration is minimized using a deformable optical element in the state in which the pupil has dilated.

As illustrated in FIG. 6(a), in the state in which the pupil has contracted, among light being incident in parallel from infinity and passing through the correction lens for correcting a diopter, that is, low order aberration, light in a peripheral portion hat has deviated from the center of the cornea is blocked, while light that passes through the center of the cornea is well focused on the retina.

As illustrated in FIG. 6(b), in the state in which the pupil has dilated, among light passing through the correction lens for correcting a diopter, that is, low order aberration, and only light that has passed through the center of the cornea is focused on the retina, while light that passes through the peripheral portion of the cornea is focused ahead of the retina and a foggy image is formed on the retina, thereby generating a light spreading.

FIG. 6(c) illustrates that a deformable optical element capable of correcting high order aberration is disposed in front of the correction lens for correcting low order aberration unlike in FIG. 6(b). In FIG. 6(c), a relatively clear image can be focused on the retina in the state in which the pupil has dilated because both the low order aberration and high order aberration of an eyesight optical system for forming eyesight of an eyeball can be corrected.

Figure 7:
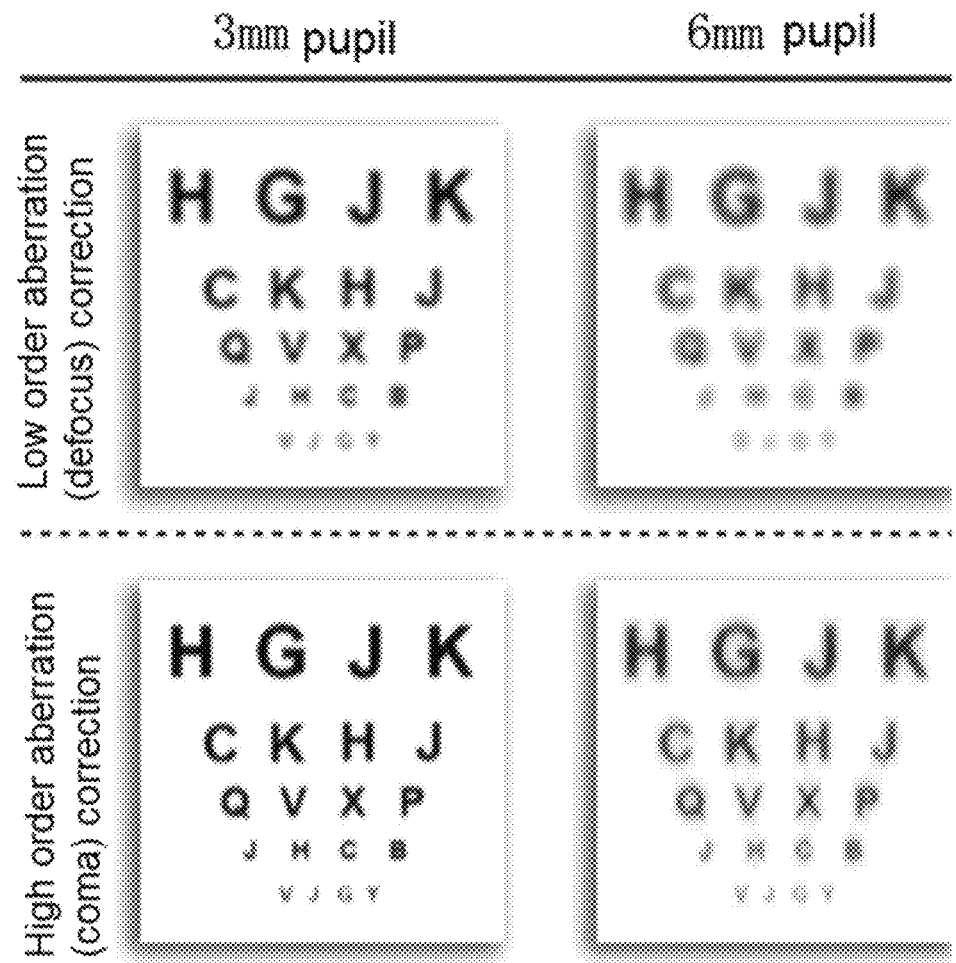
FIG. 7 is a diagram illustrating a comparison between an chart image according to the state of the pupil when only low order aberration is corrected using the deformable optical element and an chart image according to the state of the pupil when both low order aberration and high order aberration are corrected using the deformable optical element.

FIG. 7 is a diagram illustrating a comparison between an chart image according to the state of the pupil when only low order aberration is corrected using the deformable optical element and an chart image according to the state of the pupil when both low order aberration and high order aberration are corrected using the deformable optical element. Figures on the left side of FIG. 7 illustrate the state in which the pupil is open by 3 mm, that is, the state in which the pupil has contracted, and figures on the right side of FIG. 7 illustrates the state in which the pupil is open by 6 mm, that is, the state in which the pupil has dilated.

After defocus (or a diopter), that is, low order aberration, is corrected, an image of the chart is dearly focused on the retina (refer to a figure on the upper left side of FIG. 7) in the state in which the pupil has contracted, whereas a foggy image of the chart is focused on the retina (refer to a figure on the upper right side of FIG. 7) in the state in which the pupil has dilated.

After coma, that is, high order aberration, is corrected, an image of the chart is more clearly focused on the retina (refer to a figure on the lower left side of FIG. 7) in the state in which the pupil has contracted, whereas in the state in which the pupil has dilated, a clearer image of the chart is focused on the retina (refer to a figure on the lower right side of FIG. 7) compared to the case where only low order aberration has been corrected in the state in which the pupil has contracted.

Figure 8:
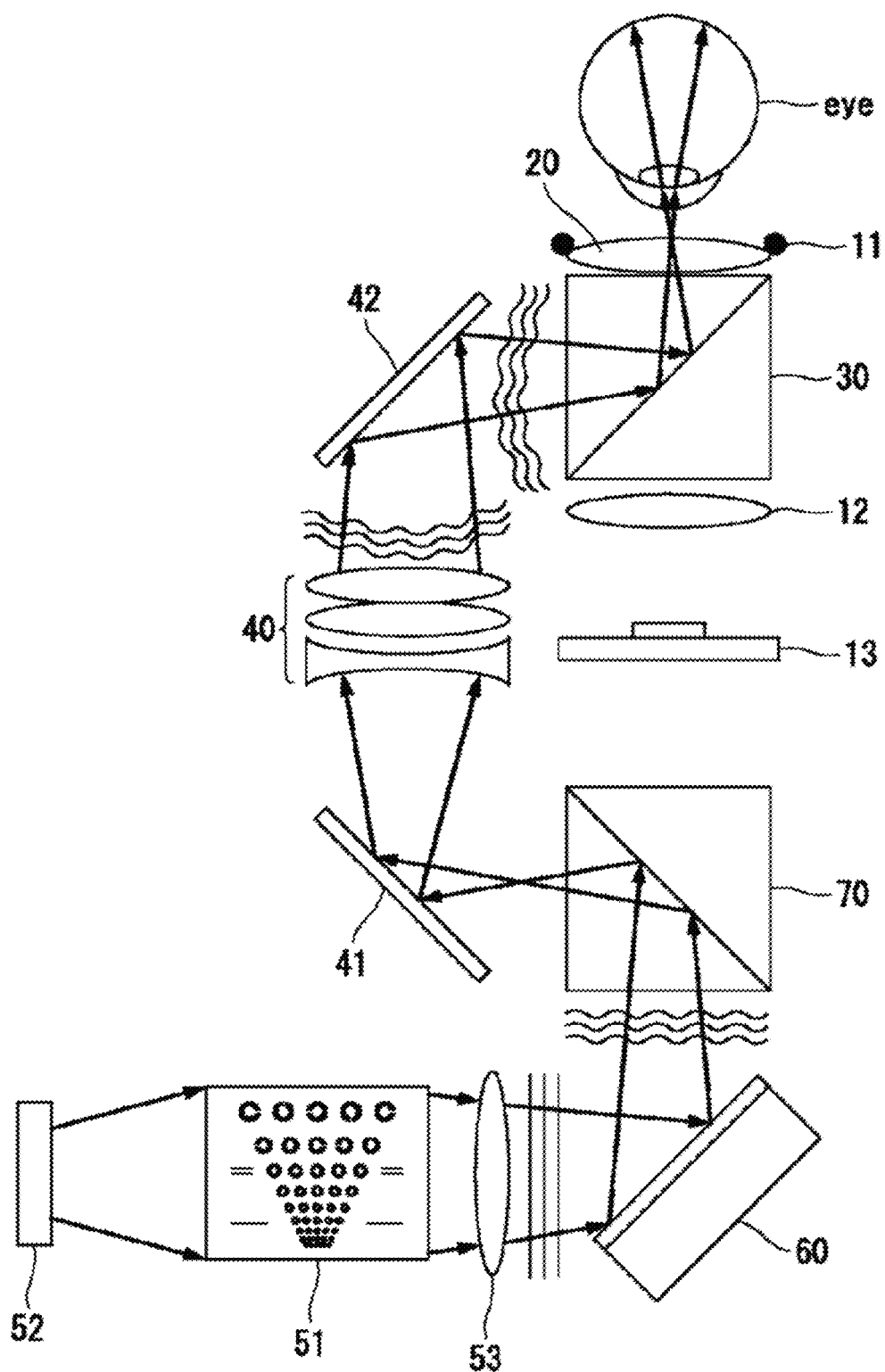
FIG. 8 is a diagram illustrating the configuration of a visual simulator configured to correct high order aberration in an eyeball using an adaptive optics element.

FIG. 8 is a diagram illustrating the configuration of a visual simulator configured to correct high order aberration in an eyeball using an adaptive optics element. The visual simulator of FIG. 8 is similar to that of FIG. 2 including the alignment optical system and the focusing optical system except that it further includes some elements, that is, four mirrors (including deformable mirror) for bending the path of light and the beam splitter 30 reflecting a visible ray and transmitting infrared rays.

The visual simulator of FIG. 8 may be configured to include an alignment optical system and a focusing optical system. The alignment optical system may include pieces of alignment lighting 11, a focusing lens 12, and a light detection element 13. The focusing optical system may be configured to correct a chart image in accordance with aberration in an eyeball and to focus the image on the retina of the eyeball. The wavefront aberration of both eyes may be previously measured through a wavefront aberration analyzer and may be stored in the memory of the visual simulator in a coefficient form.

The focusing optical system of the visual simulator of FIG. 8 may be configured to include an object lens 20, a beam splitter 30, a correction lens 40 configured to control eyesight of the eyeball, a chart-projecting unit 50 configured to output the chart light including an image of the chart, and a plurality of reflection mirrors 41, 42, 60, and 70 configured to change the path of the chart light output by the chart-projecting unit 50. The beam splitter 30 is configured to transmit reflected light of infrared rays which are radiated by the pieces of alignment lighting 11 and are reflected from the cornea of the eyeball and configured to reflect chart light of a visible ray including an image of the chart that will be focused on the retina of the eyeball.

The reflection mirrors may include mirrors 41 and 42 and a second beam splitter 70 configured to simply change the direction and a deformable mirror 60 configured to correct high order aberration In FIG. 8, chart light output from the chart-projecting unit 50 has been illustrated in the form of a plane wave. Chart light reflected from the deformable mirror 60 configured to incorporate low order aberration and high order aberration into the chart light includes a high order aberration component, but has been illustrated as having a wavefront parallel to a temporally adjacent wavefront. The wavefront of chart light that passes through the correction lens 40 has been illustrated as being greatly bent because the defocusing of low order aberration is incorporated into the chart light.

By changing chart light by incorporating the low order aberration and high order aberration of the eyeball into the chart light through the correction lens 40 and the deformable mirror 60, an image of the chart that does not contain distortion according to wavefront aberration in the eyeball is focused on the retina of the eyeball.

In order to expand the correction range of a diopter corresponding to the low order aberration of the eyeball, a zoom lens may be used along with the correction lens 40 or may be used instead of the correction lens 40. The low order aberration of the eyeball may be corrected by the deformable mirror 60 as well as the correction lens 40.

Figure 9:
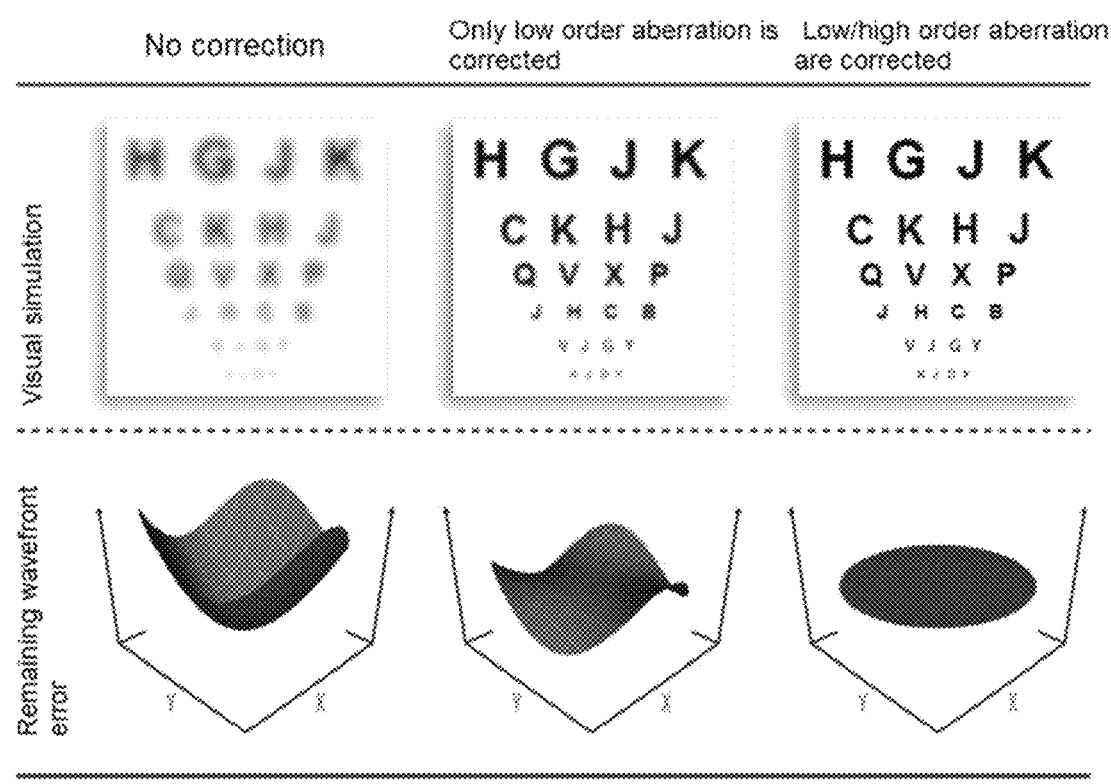
FIG. 9 is a diagram illustrating a comparison between images of the charts whose aberration of eyeballs have been corrected through a correction lens and a deformable mirror.

FIG. 9 is a diagram illustrating a comparison between images of the charts whose aberration of eyeballs have been corrected through the correction lens 40 and the deformable mirror 60. Figures on the upper side of FIG. 9 illustrate images of the chart that are focused on the retina, and figures on the lower side of FIG. 9 are graphs illustrating the remaining wavefront aberration.

If correction is not performed, an image of the chart is focused on the retina in a foggy state out of focus, and each of the frequency components of the remaining wavefront aberration is great in the XY space frequency plane, as can be seen from a figure on the leftmost side of FIG. 9. If only low order aberration is corrected through the correction lens 40, an image of the chart becomes clear compared to the case where correction is not performed, but is not sharp and the amplitude of a central part (corresponding to a low order aberration component) in the XY space frequency plane is reduced because the low order aberration component of the remaining wavefront aberration is reduced, as can be seen from a figure in the middle of FIG. 9. If both low order aberration and high order aberration are corrected through the correction lens 40 and the deformable mirror 60, an image of the chart is focused on the retina in a clear state and is displayed in a plane form in the XY space frequency plane without almost including the remaining aberration, as can be seen from a figure on the rightmost side of FIG. 9.

Figure 10:
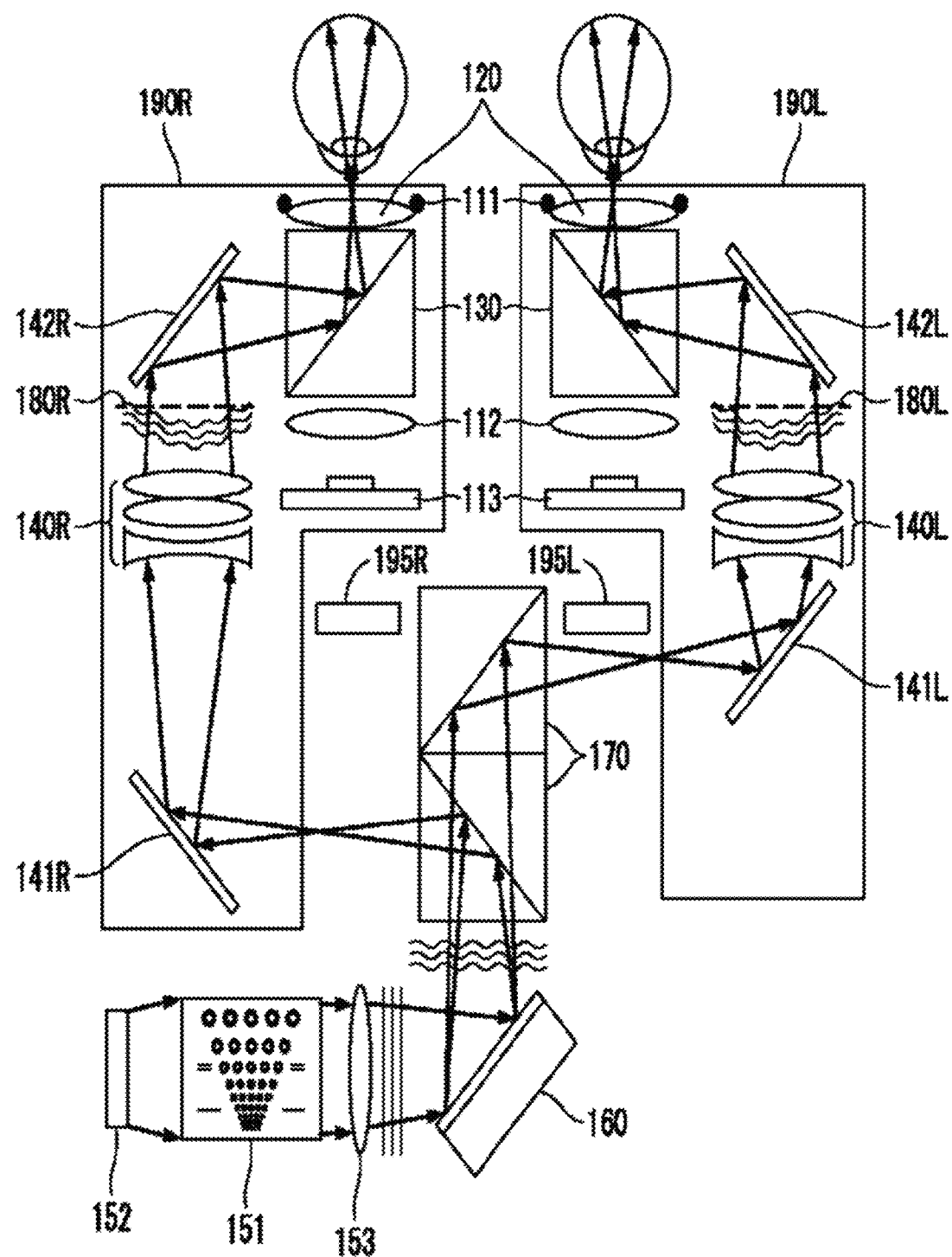
FIG. 10 is a diagram illustrating the optical elements of a binocular visual simulator in accordance with an embodiment of the present invention.

FIG. 10 is a diagram illustrating the optical elements of a binocular visual simulator in accordance with an embodiment of the present invention.

The binocular visual simulator 200 in accordance with an embodiment of the present invention may be configured to include a chart-projecting unit 150, an adaptive optics element 160, a left eye correction unit 190L, a right eye correction unit 190R, and a 2-reflected surface beam splitter 170. The chart-projecting unit 150 is configured to output chart light including a chart image. The adaptive optics element 160 is configured to change the chart light of the chart-projecting unit 150 in accordance with wavefront aberration measured with respect to a left eye and a right eye. The left eye correction unit 190L is configured to change the chart light from the adaptive optics element 160 in accordance with a low order aberration component (i.e., a diopter) corresponding to the wavefront aberration of the left eye so that an image of the chart light is focused on the retina of the left eye. The right eye correction unit 190R is configured to change the chart light from the adaptive optics element 160 in accordance with a low order aberration component corresponding to the wavefront aberration of the right eye so that an image of the chart light is focused on the retina of the right eye. The 2-reflected surface beam splitter 170 is configured to split the chart light from the adaptive optics element 160 into the left eye correction unit 190L and the right eye correction unit 190R.

Furthermore, the binocular visual simulator 200 in accordance with an embodiment of the present invention may be configured to further include a left eye correction unit transfer part 195L configured to transfer the left eye correction unit 190L in order to align the chart light with the left eye and a right eye correction unit transfer part 195R configured to transfer the right eye correction unit 190R in order to align the chart light with the right eye.

The chart-projecting unit 150 includes a chart 151, a chart lighting 152, and a chart lens 153 and is substantially the same as those of FIGS. 3 and 8.

The adaptive optics element 160 includes a plurality of actuators which are distributed on its plane and configured to be movable in a direction vertical to a surface of the mirror, like the deformable mirror, and may change the wavefront of incident light by randomly changing a displacement of a surface of the mirror. The adaptive optics element 160 may change incident chart light so that the high order aberration and/or low order aberration of light emitted from an eye (i.e., aberration of the eyesight optical system that determines eyesight of the eye) may be corrected.

The adaptive optics element 160 of the present invention may repeatedly perform an operation for changing the wavefront of chart light in accordance with the aberration of a left eye for a specific time and then changing the wavefront of the chart light in accordance with the aberration of a right eye for a specific time. The specific time may be 10 ms or less in order for an image of the chart, for example, 50 frames per second to be focused on each eye.

The 2-reflected surface beam splitter 170 splits the chart light, having a low order aberration component and/or a high order aberration component changed by the adaptive optics element 160 in accordance with the low order aberration and/or high order aberration of the eyeball, into the left eye correction unit 190L and the right eye correction unit 190R. The 2-reflected surface beam splitter 170 may include a half mirror configured to have reflexibility of about 50% and a total reflection mirror configured to totally reflect light passing through the half mirror. The half mirror and the total reflection mirror may form an angle of about 90 degrees.

A correction unit 190 (190L, 190R) may include an alignment optical system configured to align an eyeball and the correction unit 190, an optical system configured to change a low order aberration component of chart light so that an image of the chart light is focused on the retina of the eyeball, and a shutter 180 (180R, 180L). The alignment optical system includes pieces of alignment lighting 111, a focusing lens 112, and a light detection element 113 as in FIG. 8. The optical system configured to change chart light may include an object lens 120, a beam splitter 130, a correction lens 140 (140R. 140L), and two reflection mirrors 141 (140R, 140L) and 142 (142R, 142L) configured to change the path of light, and some elements of the optical system are the same as those of FIG. 8. The shutter 180 allows chart light to proceed to the eyeball when it becomes an on state or prevents chart light from proceeding to the eyeball when it becomes an off state. The shutters 180L of the left correction unit 190L and 180R of the right correction unit 190R alternately become the on state and the off state. Accordingly, a low order aberration component of chart light whose high order aberration component and/or low order aberration component has been changed by the deformable mirror 160 is additionally changed by the correction unit 190, and thus an image of the chart light is projected onto the left eye and the right eye in a time-dividing way.

Figure 11:
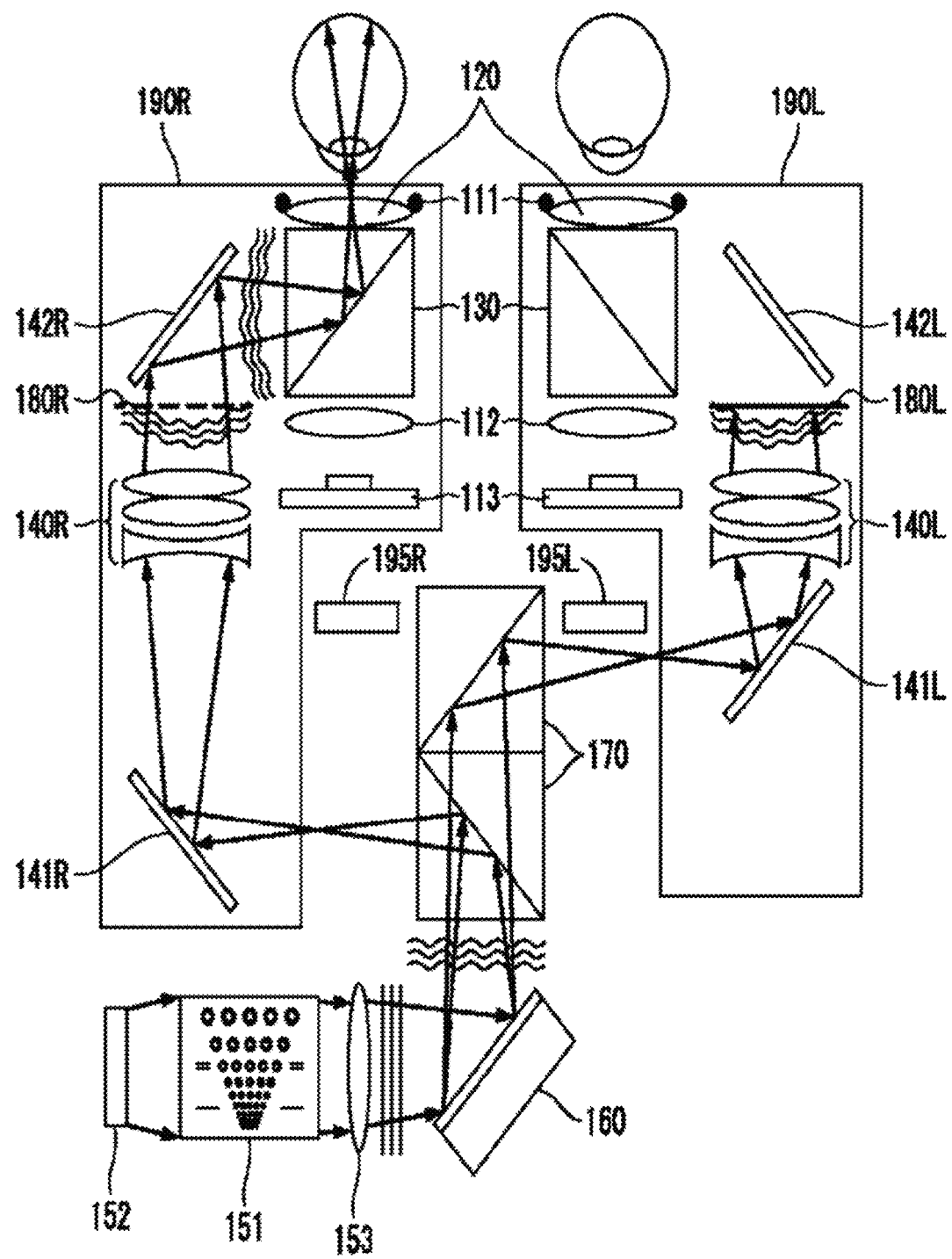
FIG. 11 illustrates the state in which the binocular visual simulator in accordance with an embodiment of the present invention forms an chart image on a right eye.

As illustrated in FIG. 11, the shutter 180R of the right eye correction unit 190R is open (i.e., maintains the on state) while the adaptive optics element 160 changes the high order aberration component of chart light on the basis of wavefront aberration in the right eye, so that an image of the chart light additionally changed by the correction lens 140R in accordance with the low order aberration component of the wavefront aberration of the right eye is focused on the retina of the right eye. In the meantime, the shutter 180L of the left eye correction unit 190L may maintain the off state so that the chart light changed by the adaptive optics element 160 on the basis of the wavefront aberration of the right eye does not enter the left eye.

Figure 12:
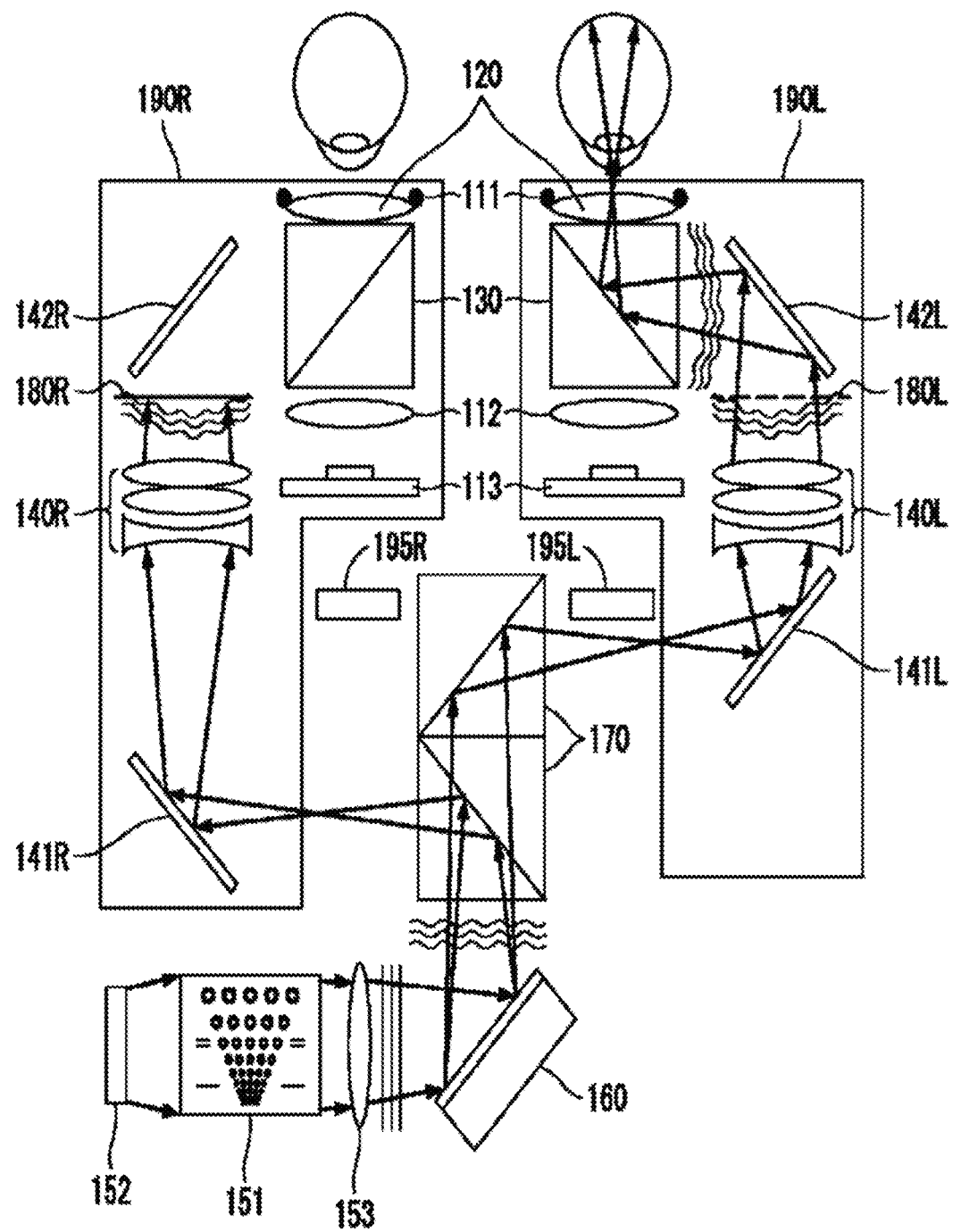
FIG. 12 illustrates the state in which the binocular visual simulator in accordance with an embodiment of the present invention forms an chart image on a left eye.

In contrast, as illustrated in FIG. 12, the shutter 180L of the left eye correction unit 190L is open (i.e., maintains the on state) while the adaptive optics element 160 changes the high order aberration component of chart light on the basis of wavefront aberration in the left eye, so that an image of the chart light additionally changed by the correction lens 140L in accordance with the low order aberration component of the wavefront aberration of the left eye is focused on the retina of the left eye. In the meantime, the shutter 180R of the right eye correction unit 190R may maintain the off state so that the chart light changed by the adaptive optics element 160 on the basis of the wavefront aberration of the left eye does not enter the right eye.

The correction lens 140 of the correction unit 190 may correct a diopter, that is, the low order aberration component of the wavefront aberration of a corresponding eyeball, by additionally changing chart light changed by the adaptive optics element 160 (or the deformable mirror) in accordance with the high order aberration component of the wavefront aberration of the corresponding eyeball (or additionally changed in accordance with some of the low order aberration component). The correction lens 140 may have a plurality of lenses configured in a zoom lens form so that the diopter (or defocusing) is controlled.

The correction lens 140 has only to maintain a state (i.e., a combination of the locations of a plurality of lenses) in which only the low order aberration component of the wavefront aberration of a corresponding eyeball is corrected because it is included in the correction unit 190 of a corresponding eyeball, regardless of whether the shutter 180 or the adaptive optics element 160 alternately operates at high speed.

It is advantageous to correct the wavefront aberration of a corresponding eyeball when the chart light output by the correction unit 190 is aligned with the center of the cornea of the corresponding eyeball. Accordingly, there is a need for means for aligning the correction unit 190 and the eyeball.

That is, the left eye correction unit 190L and the right eye correction unit 190R are physically separated from each other because they need to align the respective left and right eyeballs of an examinee and are also separated from the 2-reflected surface beam splitter 170 for splitting chart light. Thus, the locations of the left eye correction unit 190L and the right eye correction unit 190R may be independently changed. To this end, the correction unit 190 includes an alignment unit 110, and the binocular visual simulator 200 may further include the correction unit transfer part 195 (195R, 195L) configured to change the location of the correction unit 190 by moving the correction unit 190.

The alignment unit 110 may symmetrically output pieces of alignment light, each including information about an alignment index, to both eyeballs through the pieces of alignment lighting 111. Alignment light reflected from the cornea is detected through each light detection element 113. An operation unit performs signal processing on the detected alignment light. Accordingly, whether or not the center of the cornea of a corresponding eyeball is aligned with the center of a corresponding object lens 120 (or the center of chart light output by the object lens 120) may be determined in accordance with a result of the signal processing. Furthermore, whether or not the correction unit 190 (precisely, a surface of the object lens 120) and a surface of the cornea of the corresponding eyeball (i.e., the vertex of the cornea) have been separated from each other at a specific interval may also be checked based on a result of the signal processing.

The correction unit transfer part 195 may reconcile the correction unit 190 with the center of the cornea of a corresponding eyeball by transferring the correction unit 190 left or right in accordance with an alignment index image detected by the light detection element 113. For example, when the alignment lighting 111 is circular, the correction unit transfer part 195 may determine whether or not the center of circular alignment light that is reflected from the cornea of a corresponding eyeball and detected by the light detection element 113 is identical with the location of the vertex of the cornea and then determine whether the correction unit 190 and the eyeball have been aligned in accordance with a result of the determination.

Furthermore, when the pieces of alignment lighting 111 is circular, the correction unit transfer part 195 may determine whether or not the distance between the correction unit 190 and the cornea of a corresponding eyeball maintains a specific interval in accordance with the size or clear degree of circular alignment light that is reflected from the cornea and detected by the light detection element 113. The correction unit transfer part 195 may move the correction unit 190 back and forth in accordance with a result of the determination.

The correction lens 140 of the correction unit 190 may additionally control zoom magnification in accordance with the distance between the correction unit 190 and the cornea of an eyeball, for example, when the distance between the correction unit 190 and the cornea deviates from a specific interval, while correcting a diopter, that is, a low order aberration component of an eyeball. Accordingly, an element for transferring the correction unit 190 back and forth may be omitted from the correction unit transfer part 195. When the transfer of the correction unit 190 is driven only in one direction, the correction unit transfer part 195 may be configured to include a motor, a screw, and a hole for connecting the correction unit 190 to the thread or valley of the screw.

Furthermore, zoom magnification of the correction lens 140 of the correction unit 190 may be additionally changed because the distance between the chart-projecting unit 150 and the cornea of an eyeball is changed while the center of the eyeball is reconciled with the center of the object lens 120 of the correction unit 190 through the correction unit transfer part 195.

Figure 13:
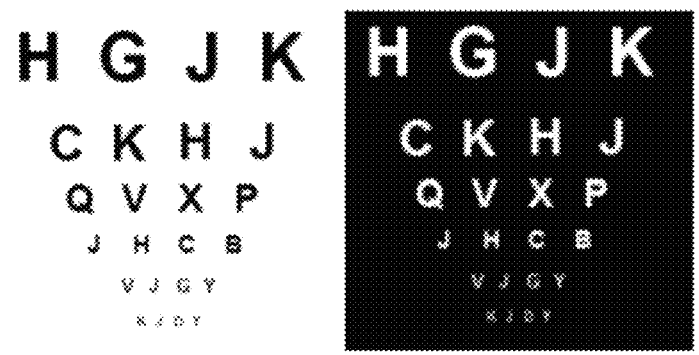
FIG. 13 is a diagram illustrating a comparison between images of charts for simulating daytime eyesight and at-night eyesight when the image of the chart is formed on the retina in the state in which the pupil has contracted and the state in which the pupil has dilated.

FIG. 13 is a diagram illustrating a comparison between images of charts for simulating daytime eyesight and at-night eyesight when the image of the chart is formed on the retina in the state in which the pupil has contracted and the state in which the pupil has dilated.

In order for at-night eyesight to be tested and for at-night eyesight after correction to be checked by a person whose eyes will be tested, it is advantageous to measure wavefront aberration of an eyeball in a dark state so that the pupil may dilate and to prepare an chart image in accordance with the measured wavefront aberration because eyesight simulations need to be performed.

If the background of an image of chart focused on the retina is bright close to white and text is dark as illustrated in a figure on the left side of FIG. 13, daytime eyesight can be simulated because the pupil contracts. If the background of an image of chart focused on the retina is dark close to black and text is bright as illustrated in a figure on the right side of FIG. 13, at-night eyesight can be simulated because the pupil dilates.

In the state in which the beam splitter is placed in the middle of a light path along which light enters an eyeball and an image of chart having a dark background has been projected, when strong light is temporarily radiated to the eyeball through the beam splitter, a person whose eyes will be tested may check whether or not a light spreading phenomenon occurs.

Furthermore, an optical system for recognizing the size of the iris may be added to the binocular visual simulator in accordance with an embodiment of the present invention in order to automatically recognize the size of the pupil and to gradually control the brightness of an chart image in accordance with the recognized size.

The binocular visual simulator in accordance with an embodiment of the present invention may be configured to include a storage unit, a driving unit, the operation unit, and the control unit configured to control the operations of the elements. The storage unit functions to store the wavefront aberration of the eyesight optical system configured to determine eyesight of both eyes. The driving unit functions to drive the correction lens 140, the chart-projecting unit 150, the deformable mirror 160, the shutter 180, the correction unit transfer part 195, and the alignment optical system. The operation unit may analyze an image detected by the light detection element 113, may calculate the distance between the correction unit 190 and the cornea of an eyeball and the location of the center of the cornea, may calculate the driving value of the correction unit transfer part 195 required for a movement of the correction unit 190 in accordance with the calculated distance and location, may calculate a high order aberration component to be compensated for through the deformable mirror 160 and a low order aberration component to be compensated for through the correction lens 140 in accordance with the wavefront aberration of the storage unit, and may calculate the driving values of the correction lens 140 and the deformable mirror 160 required to compensate for the calculated components. The wavefront aberration of the eyesight optical system may be directly delivered by the binocular visual simulator that is connected to the eyesight optical system through an interface and that is configured to measure the wavefront aberration.

Figure 14:
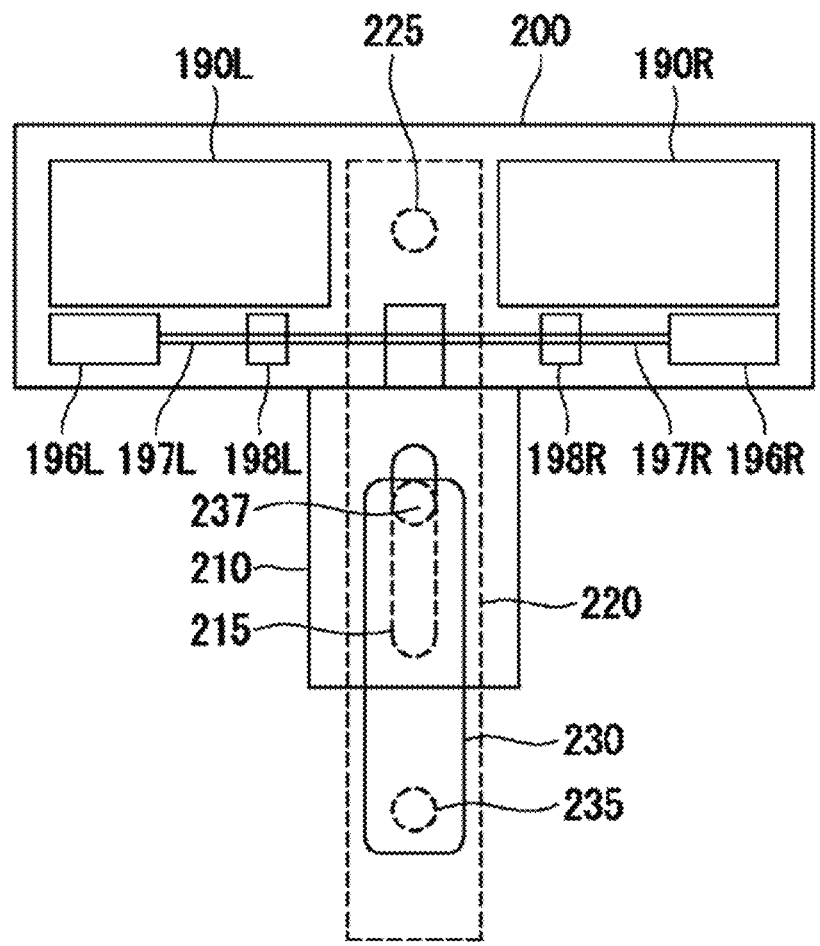
FIG. 14 is a diagram illustrating elements configured to control an eye level of the binocular visual simulator.

FIG. 14 is a diagram illustrating elements configured to control an eye level of the binocular visual simulator.

In a plane movement (i.e., right and left directions or back and forth directions) of the correction unit 190, there is changed only the length of a path until chart light outputted from a single chart-projecting unit 150 is focused on a corresponding eyeball. The change of the path length may be compensated for by the correction lens 140 including the zoom lens. Accordingly, the left eye correction unit 190L and the right eye correction unit 190R may be independently moved from side to side in accordance with the distance between a left eyeball and a right eyeball and may also be independently moved back and forth in accordance with the distance between an eyeball and the correction unit 190.

When a displacement of both eyes is horizontally changed up and down in parallel, the binocular visual simulator has only to be transferred in the height direction. However, when both eyes are tilted on the basis of a horizontal direction, it is difficult to compensate for such tilting using a simple optical element, such as a zoom lens. Accordingly, the binocular visual simulator needs to be mechanically tilted in accordance with the degree that both eyes have been tilted.

FIG. 14 is a front view of the binocular visual simulator. The binocular visual simulator may be configured to include a main body 200, a first link 210, a vertical support 220, and a second link 230. The main body 200 includes the chart-projecting unit 150, the adaptive optics element 160, the 2-reflected surface beam splitter 170, the left eye and right eye correction units 190L/190R, and the correction unit transfer part 195. The first link 210 is downward protruded from the center of the main body 200 on the basis of right and left directions. The vertical support 220 is hinged with the main body 200 and is configured to support the main body 200. The second link 230 is connected to the first link 210 and the vertical support 220.

As described above, the correction unit transfer part 195 may be configured to include a transfer motor 196 (196R, 196L) configured to generate rotatory power, such as a step motor, a screw 197 (197R, 197L) rotated by the rotatory power of the transfer motor 196 and configured to have the thread and valley of a spiral screw formed therein, and a holder 198 (198R, 198L) configured to connect the correction unit 190 to the thread or valley of the screw 197 and to transform the rotatory power of the transfer motor 196 into straight-line propulsion. When the step motor is used as the transfer motor 196, the current location of the correction unit 190 from a specific initial location may be calculated using the number of step inputs applied to the step motor. If a DC motor is used in the transfer motor 196, the location of the correction unit 190 may be calculated in accordance with an electric current applied to the DC motor and the direction of the current.

The first link 210 is downward protruded from the center of the main body 200 on the basis of the right and left directions.

A guide slot 215 of a long hole form in a height direction or a vertical direction is formed at the center of the first link 210 on the basis of the right and left directions.

The vertical support 220 is hinged with the main body 200 around a first pivot 225 that is the center of the main body 200 on the basis of the right and left directions and that is provided at a location, that is, a middle between the correction unit 190 on the basis of the vertical direction. A hole corresponding to the first pivot 225 which is formed in the vertical support 220 is formed in the main body 200 so that the vertical support 220 is hinged with the main body 200. Alternatively, a hole corresponding to the first pivot 225 which is formed in the main body 200 is formed in the vertical support 220 so that the vertical support 220 is hinged with the main body 200.

The second link 230 is hinged with the vertical support 220 on the basis of a second pivot 235 that is parallel to the first pivot 225 on the basis of the right and left directions and that is placed under the guide slot 215 on the basis of the vertical direction. The second link 230 includes a sliding member 237 to be moved under the guidance of the guide slot 215 provided in the first link 210. The second pivot 235 is formed in the second link 230 and a hope corresponding to the second pivot 235 is formed in the vertical support 220 so that the second link 230 is hinged with the vertical support 220. Alternatively, the second pivot 235 is formed in the vertical support 220 and a hole corresponding to the second pivot 235 is formed in the second link 230 so that the second link 230 is hinged with the vertical support 220.

Figure 15:
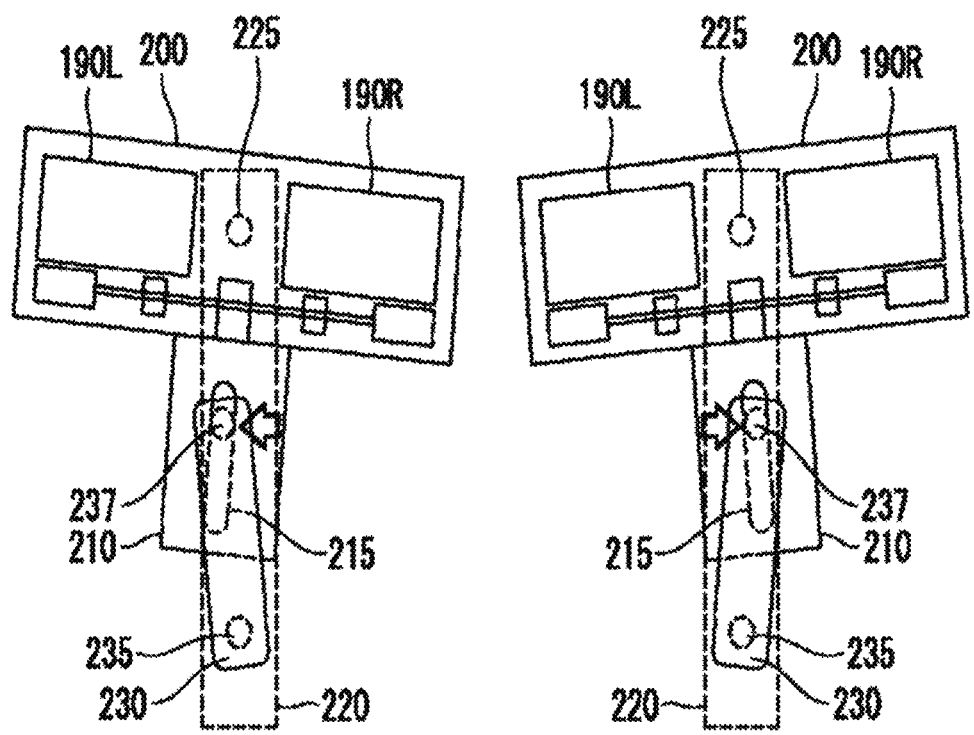
FIG. 15 is a diagram illustrating an embodiment in which the visual simulator is tilted by reconciling both eyes with a tilted state.

The sliding member 237 is protruded from the second link 230 and is inserted into the guide slot 215 provided in the first link 210, to move along the guide slot 215. As illustrated in FIG. 15, when force is applied to the second link 230 near the sliding member 237 or the sliding member 237 in the right and left directions, the location of the sliding member 237 in the guide slot 215 is changed, and thus the main body 200 is changed around the first pivot 225. As a result, the main body 200 is tilted on the basis of the horizontal direction.

FIG. 15 is a diagram illustrating an embodiment in which the binocular visual simulator is tilted by reconciling both eyes with a tilted state. The main body 200 may be tilted in accordance with the degree that both eyeballs of an examinee have been tilted by applying force to the sliding member 237 in the right and left directions.

Figure 16:
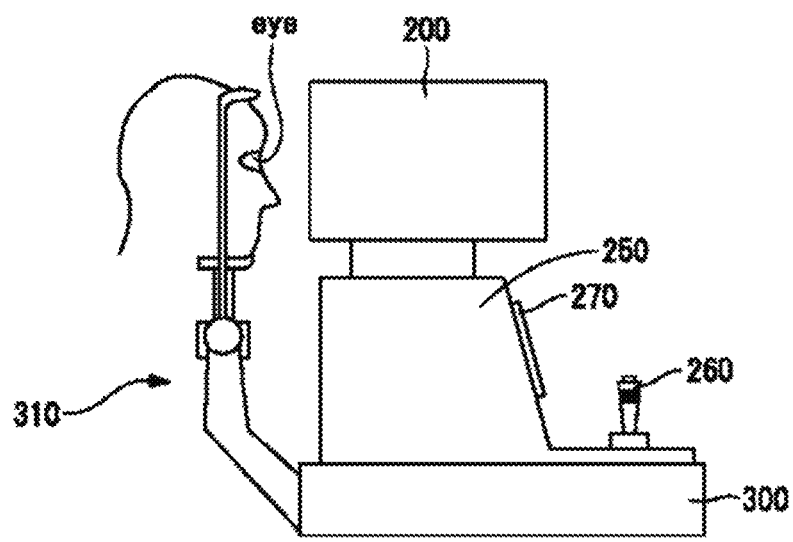
FIG. 16 schematically illustrates an overall configuration of the binocular visual simulator in accordance with an embodiment of the present invention.

FIG. 16 schematically illustrates an overall configuration of the binocular visual simulator in accordance with an embodiment of the present invention.

The binocular visual simulator may be configured to include a base 300, a face support 310 fixed to the front of the base 300 and configured to support the jaws and forehead of an examinee so that a face of the examinee is not moved, a movable stand 250 placed on the base 300 and disposed to be movable from side to side and back and forth, and the main body 200 disposed over the movable stand 250. The movable stand 250 may be moved on the base 300 from side to side and back and forth with respect to both eyes of a person whose eyes will be tested in response to a manipulation of a joystick 260. A display 270 may be mounted on the binocular visual simulator so that an operator may check the operating state of the binocular visual simulator.

The main body 200, by using the single adaptive optics element, changes pieces of chart light, including respective images of a chart to be focused on the retinas of a left eye and a right eye, based on wavefront aberrations measured with respect to the left eye and the right eye, then additionally changes the pieces of chart light by using the left eye correction unit and the right eye correction unit, and then produces the pieces of changed chart light to the left eye and the right eye.

The main body 200 may further include a mechanical element configured to tilt the main body 200 or include transfer parts configured to independently transfer the left eye and the right eye correction unit from side to side, as described with reference to FIG. 14. The vertical support 220 may be fixed to the movable stand 250.

Both faces of a person rarely form bilateral symmetry. Although a person thinks that he or she stands his or her face erect vertically, both eyes of the person may be tilted or may have different heights.

When the wavefront aberration of an eyeball is to be measured, the wavefront aberrations of a left eye and a right eye are separately measured horizontally. When the left eye and the right eye have the same height, there is no problem because the binocular visual simulator in accordance with an embodiment of the present invention is driven horizontally.

When the binocular visual simulator needs to be tilted because a left eye and a right eye have different heights, however, the binocular visual simulator is tilted and driven while both eyes remain horizontal. Accordingly, in compensating mode, it is difficult to precisely consider the aberration having directivity, for example, coma or astigmatism, among the wavefront aberrations of an eyeball.

In order to solve such a problem, the binocular visual simulator 200 in accordance with an embodiment of the present invention may further include a sensor configured to measure an angle of the correction unit 190 that is tilted by the second link 230. In this case, the binocular visual simulator 200 may measure and output a tilted direction and angle of the correction unit 190 using the sensor.

Furthermore, the control unit of the binocular visual simulator 200 in accordance with an embodiment of the present invention modifies one or more of the wavefront aberrations of a left eye and a right eye, stored in the storage unit, based on a tilt value measured by the sensor through the operation unit. In this case, the control unit may modify only an aberration component having directivity among the wavefront aberrations. Furthermore, after the wavefront aberrations of the left eye and the right eye are modified in accordance with the tilting of the correction unit 190, the control unit may change the driving value of the deformable mirror 160 in accordance with the modified wavefront aberrations.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A binocular visual simulator comprising:
a chart-projecting unit for producing a chart light including a chart image to be focused on a retina;
an adaptive optics element for changing the chart light of the chart-projecting unit in accordance with wavefront aberration measured for a left eye and a right eye;
a beam splitter for dividing the chart light changed by the adaptive optics element into two chart lights;
a left eye correction unit for changing the chart light divided by the beam splitter in accordance with wavefront aberration of the left eye so that the chart light is focused on a retina of the left eye; and
a right eye correction unit for changing the chart light divided by the beam splitter in accordance with wavefront aberration of the right eye so that the chart light is focused on a retina of the right eye,
wherein each of the left eye correction unit and the right eye correction unit includes a shutter for controlling projection of the chart light to the left eye and the right eye, and the shutter of the left eye correction unit and the shutter of the right eye correction unit are alternately turned on and turned off.

2. The binocular visual simulator as claimed in claim 1, wherein each of the left eye correction unit and the right eye correction unit includes an alignment optical system for detecting an alignment of a center of cornea of the corresponding eyeball with a center of a light outputted from the corresponding eye correction unit.

3. The binocular visual simulator as claimed in claim 2, wherein the alignment optical system includes an alignment lighting for symmetrically radiating invisible rays toward the eyeball, a beam splitter for reflecting the chart light and for transmitting a reflected light of the invisible rays reflected at the cornea of the eyeball and a light detection element for detecting the reflected light.

4. The binocular visual simulator as claimed in claim 2, wherein each of the left eye correction unit and the right eye correction unit includes an actuator for moving the corresponding eye correction unit so that the center of each cornea is aligned with a center of the light of the left eye correction unit and the right eye correction unit.

5. The binocular visual simulator as claimed in claim 1, wherein each of the left eye correction unit and the right eye correction unit includes a plurality of lenses for compensating for low order aberration of wavefront aberration which is measured for the corresponding eyeball.

6. The binocular visual simulator as claimed in claim 5, wherein the plurality of lenses is a zoom lens for controlling a defocusing of incident light.

7. The binocular visual simulator as claimed in claim 6, wherein the zoom magnification of the zoom lens is additionally controlled in accordance with a distance between the corresponding eye correction unit and the corresponding cornea of an eyeball.

8. The binocular visual simulator as claimed in claim 6, wherein the zoom magnification of the zoom lens is additionally controlled in accordance with a distance between the beam splitter and the corresponding eye correction unit in left and right direction.

9. The binocular visual simulator as claimed in claim 1, wherein the adaptive optics element compensates for high order aberration among the wavefront aberrations measured for the left eye and the right eye, thereby changing a wavefront of the chart light.

10. The binocular visual simulator as claimed in claim 9, wherein the adaptive optics element is a deformable mirror whose surface is changed by a plurality of actuators.

11. The binocular visual simulator as claimed in claim 9, wherein the adaptive optics element is operated with being synchronized with the shutter of the left eye correction unit and the shutter of the right eye correction unit.

12. The binocular visual simulator as claimed in claim 11, wherein the adaptive optics element operates in accordance with the wavefront aberration of the left eye when the shutter of the left eye correction unit is open and the adaptive optics element operates in accordance with the wavefront aberration of the right eye when the shutter of the right eye correction unit is open.

13. The binocular visual simulator as claimed in claim 1, wherein the chart-projecting unit produces either the chart light including a chart image in which black letters are on white background or the chart light including a chart image in which white letters are on black background.

14. A binocular visual simulator comprising:
- a main body including an adaptive optics element for changing a chart light including chart images to be focused on retinas of a left eye and a right eye in accordance with wavefront aberration measured for the left eye and the right eye, and a left eye correction unit and a right eye correction unit for further changing the chart light and projecting the changed chart lights to a retina of the left eye and a retina of the right eye, respectively;
- a first link downwardly extended from the center of the main body and having a guide slot formed in the first link;
- a vertical support hingedly connected to the main body; and
- a second link hingedly connected to the vertical support and having a sliding member being moved along the guide slot.

15. The binocular visual simulator as claimed in claim 14, wherein the vertical support is hingedly connected to the main body at a first position that is a center of the main body in the right and left directions and that is a center of the left eye correction unit and the right eye correction unit in the vertical direction.

16. The binocular visual simulator as claimed in claim 14, wherein the guide slot is formed in a vertically extended shape.

17. The binocular visual simulator as claimed in claim 16, wherein when the sliding member moves in the right and left directions along the guide slot, the main body is tilted from horizontal position.

18. The binocular visual simulator as claimed in claim 14, further comprising a left transfer part for moving the left eye correction unit in the left and right directions; and a right transfer part for moving the right eye correction unit in the left and right directions.

19. The binocular visual simulator as claimed in claim 18, wherein the left transfer part and the right transfer part are linearly actuated by a screw rotated by a rotator motor.

20. The binocular visual simulator as claimed in claim 14, further comprising a base; and a movable stand which moves in a horizontal direction on the base, and the base comprises a face support for supporting a forehead and jaw of a person, and the vertical support is fixed to the movable stand.

21. The binocular visual simulator as claimed in claim 14, further comprising a sensor for measuring an angle and direction of the left eye correction unit and/or the right eye correction unit which are tilted by the second link.

22. The binocular visual simulator as claimed in claim 14, wherein the wavefront aberration of the left eye and/or the right eye is modified in accordance with the angle and direction measured by the sensor, and the chart light is changed in accordance with the modified wavefront aberration.

\* \* \* \* \*